United States Patent
Khrimian et al.

(10) Patent No.: US 6,469,219 B1
(45) Date of Patent: Oct. 22, 2002

(54) PRODUCTION OF FLUOROMETHYL 2,2,2-TRIFLUORO-1-(TRIFLUOROMETHYL) ETHYL ETHER

(75) Inventors: Achot Pavlikovich Khrimian, North Augusta, SC (US); Barry Malcolm Jones, North Augusta, SC (US)

(73) Assignee: Halocarbon Products Corporation, River Edge, NJ (US)

( * ) Notice: Subject to any disclaimer, the term of this patent is extended or adjusted under 35 U.S.C. 154(b) by 0 days.

(21) Appl. No.: 09/527,045

(22) Filed: Mar. 16, 2000

(51) Int. Cl.[7] .......................... C07C 41/09; C07C 41/34
(52) U.S. Cl. ........................ 568/683; 568/693
(58) Field of Search ................... 568/683, 698; 252/1; 423/483

(56) References Cited

U.S. PATENT DOCUMENTS

| | | | | |
|---|---|---|---|---|
| 2,992,276 A | * | 7/1961 | Weinmayr | 260/614 |
| 3,683,092 A | * | 8/1972 | Regan et al. | 424/342 |
| 3,689,571 A | * | 9/1972 | Regan et al. | 260/614 F |
| RE29,084 E | * | 12/1976 | Anderson et al. | 585/706 |
| 4,250,334 A | * | 2/1981 | Coon et al. | 568/683 |
| 4,314,087 A | * | 2/1982 | Radlick | 568/400 |
| 4,469,898 A | * | 9/1984 | Coon et al. | 568/683 |
| 5,679,576 A | * | 10/1997 | Kawai et al. | 436/55 |
| 5,969,193 A | * | 10/1999 | Terrell | 568/683 |
| 5,990,359 A | * | 11/1999 | Ryan et al. | 568/683 |

FOREIGN PATENT DOCUMENTS

WO     93/12057    * 6/1993

OTHER PUBLICATIONS

Perrin et al., Purification of Laboratory Chemicals, second edition, p. 556, 1980.*

* cited by examiner

Primary Examiner—Rosalynd Keys
(74) Attorney, Agent, or Firm—Norris McLaughlin & Marcus

(57) ABSTRACT

An improved process for preparing fluoromethyl 2,2,2-trifluoro-1-(trifluoromethyl)ethyl ether(sevoflurane) by reacting 1,1,1,3,3,3-hexafluoro-2-propanol with formaldehyde and hydrogen fluoride either A) under distillation conditions or B) in the presence of or with the subsequent addition of a solvent capable of selectively extracting sevoflurane.

41 Claims, No Drawings

PRODUCTION OF FLUOROMETHYL 2,2,2-TRIFLUORO-1-(TRIFLUOROMETHYL) ETHYL ETHER

BACKGROUND OF THE INVENTION

1. Field of the Invention

The present invention is a method of preparing the inhalation anesthetic, fluoromethyl 2,2,2-trifluoro-1-(trifluoromethyl)ethyl ether (also known as sevoflurane), by an equilibrium process wherein the equilibrium is favorably shifted by removal of the product by distillation under active equilibrium conditions or by extraction of the product from the equilibrium mixture. This method is based on commercially available starting materials, produces higher yields of the desired product, and is more economical than prior art methods.

2. Description of Related Art

A number of methods have been disclosed for preparing sevoflurane (SVF). U.S. Pat. No. 3,683,092 and 3,689,571 describe the replacement of chlorine in chloromethyl 2,2,2-trifluoro-1-(trifluoromethyl)ethyl ether with fluorine using potassium fluoride in a solvent, sulfolane, at 120° C., and U.S. Pat. No. 4,874,901 discloses the replacement without added solvent at high temperature (185° C.) and pressure (280 psi). Other fluorinating reagents were also used to replace the chlorine. U.S. Pat. No. 5,886,239 uses diisopropylethylamine hydrofluoride, and the European Patent Appl. EP 0 901 999 A1 uses a mixture of an amine and hydrogen fluoride (HF). The starting material, chloromethyl 2,2,2-trifluoro-1-(trifluoromethyl)ethyl ether, is not commercially available. According to U.S. Pat. No. 3,683,092 it is prepared by the chlorination of methyl 2,2,2-trifluoro-1-(trifluoromethyl)ethyl ether, which can be synthesized from 1,1,1,3,3,3-hexafluoro-2-propanol, as described in U.S. Pat. No. 3,911,024.

Direct fluorination of methyl 2,2,2-trifluoro-1-(trifluoromethyl)ethyl ether to SVF is claimed using extremely reactive and expensive reagents such as bromine trifluoride in U.S. Pat. No. 3,683,092, and 20% molecular fluorine in argon in U.S. Pat. No. 3,897,502.

Another route to SVF, disclosed in U.S. Pat. No. 4,874,902, uses 1,1,1,3,3,3-hexachloro-2-propanol as starting material which is converted to methyl 2,2,2-trichloro-1-(trichloromethyl)ethyl ether, and then fluorinated with bromine trifluoride to give SVF. Alternatively, methyl 2,2,2-trichloro-1-(trichloromethyl)ethyl ether is chlorinated, and the corresponding chloromethyl ether is multipli-fluorinated using bromine trifluoride.

U.S. Pat. No. 5,705,710 describes preparation of SVF by fluorination of methoxymalononitrile using bromine trifluoride.

The above-mentioned methods of preparation of SVF are multi-step, or based on commercially unavailable starting materials, or use dangerous reagents.

Direct fluoromethylation to SVF of commercially available 1,1,1,3,3,3-hexafluoro-2-propanol (HFIP) is described in several patents. In U.S. Pat. No. 4,250,334, HFIP, HF and formaldehyde ($CH_2O$) are heated in the presence of concentrated sulfric acid to continuously produce SVF collected in a cold trap.

According to U.S. Pat. No. 4,469,898, the yields of SVF are improved by adding excess sulfuric acid or other additives to sequester the water produced in the fluoromethylation of HFIP.

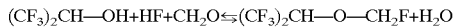

However, a substantial amount of concentrated sulfuric acid or other Bronsted and/or Lewis acid (ca. 3 times greater then HFIP by weight) should be used to achieve 76–78% yield. As a result, large amounts of wastes (inorganic and organic) are made by the process.

PCT Int. Appl. WO 97/25303 discloses preparation of SVF by the reaction of HFIP with bis(fluoromethyl)ether in the presence of sulfuric acid, in which the desired product is produced with 55–60% yield along with an acetal by-product.

If no sulfuric acid or dehydrating, protonating and fluoride ion generating agent is used, the yields of SVF were very low, as was shown in the abandoned U.S. patent application Ser. No. 771,365, filed Oct. 28, 1968, and also in U.S. Pat. No. 3,689,571.

SUMMARY OF THE INVENTION

The present invention provides a method for the preparation of SVF by reacting HFIP with $CH_2O$ and HF under conditions wherein the desired product SVF is removed from the ongoing equilibrium either A) by distillation or B) by extraction.

A low-boiling azeotrope of SVF and HF was discovered so where SVF is removed by distillation, it is removed as an azeotrope with HF. During this process, water is also removed by distillation of the constant boiling mixture of water and HF (b.p. 115° C.). SVF, removed as the HF azeotrope, is separated from HF by several methods: (i), washing the mixture with water, (ii), extracting with solvents dissolving SVF but not HF, (iii), cooling the azeotrope to separate layers, and (iv), distilling the SVF/HF azeotrope at the different pressures to obtain a mixture enriched in SVF.

In the extraction process, SVF is removed from the equilibrium by a solvent capable of selectively dissolving SVF and other reaction products but not starting materials and water.

DETAILED DESCRIPTION OF THE INVENTION

1. Removal of SVF by Distillation during Reaction

One preferred embodiment of the invention involves running the fluoromethylation reaction during distillation. This is accomplished by having a reactor equipped with two columns. One is used to separate, as an overhead product, the HF/SVF mixture from the vapor over the equilibrium mixture. We discovered that SVF and HF form the low-boiling azeotrope described in Table 4. The other column is fed from the liquid in the reactor and removes the HF/water constant boiling mixture as a bottoms product. The overhead distillate from this second column is recycled to the reactor.

In practice, the HF/SVF azeotrope distillate may contain excess HF because the azeotrope boils only slightly lower than HF. [The use of the words SVF/HF azeotrope throughout the text is meant to include the actual azeotrope and the azeotrope when it includes excess HF.] The overhead from the first column, which is called "HF/SVF azeotrope" will proceed to one of several separation methods to obtain pure SVF and return HF to the reaction/distillation process.

A. Separation of the HF/SVF Azeotrope to Obtain Pure SVF

The HF/SVF azeotrope can be separated very simply by washing the HF out with water. The SVF has a purity of about 99%.

As an alternative to water, SVF can be separated from HF by extraction with a large variety of suitable solvents, which are insoluble in hydrogen fluoride (see Section 2, infra). Following the extraction of SVF, HF can be recycled to the reaction and the SVF can be separated from the solvent and purified to the desired purity.

Another approach to separating SVF from HF is to cool the mixture. Upon cooling, separation begins at a lower temperature depending upon the composition of the HF/SVF mixture. The SVF/HF ratios are different in each layer. The separated layer with the enriched SVF can be distilled to obtain the SVF/HF azeotrope as the lower boiling product and excess SVF as the higher boiling product. The layer enriched in HF can be returned to the reaction/distillation process.

Still another means of separating SVF/HF is by varying the composition of the SVF/HF azeotrope through the use of different pressures (Table 4). An azeotropic composition that has a higher SVF content can be distilled at a different pressure to give an azeotrope containing less SVF as the lower boiling product and the excess SVF as the pure higher boiling product.

B. Recovery of Byproducts

Four major byproducts: bis{[2,2,2-trifluoro-1-(trifluoromethyl)ethoxy]methyl}ether (compound A), formaldehyde di[2,2,2-trifluoro-1-(trifluoromethyl)ethyl]acetal (compound B), formaldehyde fluoromethyl[2,2,2-trifluoro-1-(trifluoromethyl)ethyl]acetal (compound C), and bis (fluoromethyl) ether (compound D) were found. In a batch run it was found that their concentrations decreased to almost undetected levels by the end of distillation. All four compounds will react as well during a continuous distillation generating additional SVF by way of the following equilibria.

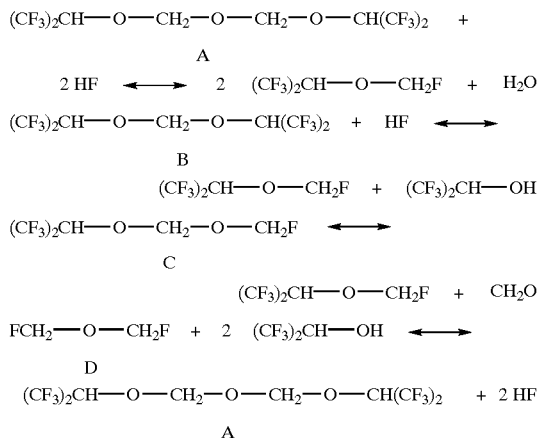

These byproducts are reported in the literature (U.S. Pat. Nos. 3,689,571 and 4,469,898, Int. Appl., WO 97/30961, and Int. Appl. WO 97/25303) where they were used as a source of SVF.

In view of the chemistry described above, it is obvious that polyethers of general formula $R_1O(CH_2O)nR_2$, in which n is a small number and $R_1$ and $R_2$ are hydrogens, alkyl groups, or haloalkyl groups, but both R1 and R 2 are not hydrogens in one formula, will revert to their starting materials under reaction/distillation conditions. Where the haloalkyl group is 1,1,1,3,3,3-hexafluoro-2-propyl SVF will be formed.

C. General Conditions

It will be obvious to those skilled in the art that this distillation under reaction conditions can be done either in a batch manner or continuously. Under continuous conditions the reactants would be added to the distillation system with the amounts of new components reduced by the amounts of reactants being continuously recycled. The reaction/distillation should be run continuously with columns capable of separating the SVF azeotrope from the other reactants and the constant boiling mixture of water and HF and of sufficient size, including the reboiler, to maintain the throughput desired. In this process, the equipment associated with the separation of HF and SVF would also provide the pure SVF and streams for recycle continuously. Conditions should be adjusted so they are close to optimum for both reaction and distillation.

The reaction should be conducted with the stoichiometric excess of HF in order to drive the equilibrium forward, and to provide for the HF/SVF and HF/H$_2$O azeotropes. The process runs well with 15–18, or preferably with 25–30 mole equivalents of HF to HFIP.

The term "formaldehyde" (CH$_2$O) as used throughout this application, unless otherwise noted, is intended to include formaldehyde polymers, such as trioxane, which is preferred, and paraformaldehyde.

The reaction temperature is not critical, but the yields are substantially improved above 50° C. Preferably, the reactive distillation can be conducted under autogenous pressure of 30–40 psig ensuring pot temperatures 45–75 ° C.

2. Removal of SVF by Extraction during Reaction

In a second preferred embodiment, the invention involves extracting the SVF product from the reaction mixture during the ongoing reaction.

The requirements for suitable solvents for this extraction are as follows:

1. The solvent should selectively extract SVF from the fluoromethylation mixture and not extract HFIP.
2. It should be hydrophobic.
3. It should not extract substantial amounts of HF.
4. It should not extract substantial amounts of CH$_2$O or its polymeric forms.
5. The solvent should be easily separable from SVF.

A. Suitability of Various Solvents to Extract SVF

Several non-polar solvents have been evaluated for their ability to extract SVF and HFIP from HF. The partitions of SVF and of HFIP in solvent/HF system were measured by mixing a small amount of either SVF or HFIP with a two-layer mixture of equal volumes of a particular solvent and HF at 25° C. After enough mixing to reach equilibrium, the fraction of original compound found in the solvent was determined by Gas Chromatography (GC) and quantified using standards. The data are given in Table 1.

TABLE 1

Partition Coefficients of SVF and HFIP in solvent/HF system

| Compound | HC-0.8 oil[a] | 1,2,3-trichloropropane | Isooctane | Krytox[b] | Perfluoro-methyldecalin |
|---|---|---|---|---|---|
| SVF | 1.00 | 0.45 | 0.30 | 0.32 | 0.22 |
| HFIP | 0.01 | <0.005 | <0.005 | <0.005 | <0.005 |

[a]Mixture of tetrachlorohexafluorobutanes, commercially available as HC-0.8 oil from Halocarbon Products Corporation
[b]1:1 mixture of DuPont Krytox GLP 100 and K6

As Table 1 demonstrates, a large variety of solvents are capable of extracting SVF from HF. Of these solvents it appears that the HC-0.8 oil is superior. On the other hand, none of the solvents studied extracted any significant amounts of HFIP from HF. From these data would appear that CFC solvents would also be good candidates for extraction. Hence, chlorofluorocarbons, chlorohydrocarbons, perfluorohydrocarbons, perfluoroethers, hydrocarbons and other solvents satisfying the requirements mentioned above are expected to be suitable for shifting the equilibrium.

B. General Conditions

While the order of addition of reactants is not critical, the reaction was conducted by adding HFIP to the mixture of anhydrous HF, formaldehyde and HC-0.8 under agitation. SVP and other products (see below) were extracted by the solvent. The layers were separated and more HC-0.8 oil was added and the reaction was continued until no further progress was seen.

The reaction temperature is not critical, but the reaction time and yields were substantially improved above 50° C. Preferably, the reaction temperature should be maintained 60–70° C. To achieve high conversion, both HF and $CH_2O$ should be present in excess of HFIP. Preferably, 50–100% molar excess of $CH_2O$, and up to 1000 molar excess HF were used.

The amount of solvent to be used for extraction is not important because it could be easily recycled after distilling SVF. In batch reactions the frequency of extractions is an important factor to efficiently shift the equilibrium and shorten reaction time. Ideally, the process should be conducted under continuous extraction conditions.

As indicated previously according to U. S. Pat. No. 4,469,898, the yields of SVF are improved by adding excess sulfuric acid or other additives to sequester the water produced in the fluoromethylation of HFIP. HF is known to function as a water sequestering agent. Accordingly, the teaching of U.S. Pat. No. 4,469,898 is to employ additional water sequestering agents. It has been found that in the context of the present invention such use of additional water sequestering agents is unnecessary, and the extraction process can advantageously be carried out in the absence of a water sequestering agent other than the HF starting material.

C. Recovery of Byproducts

In addition to four major byproducts (A–D) extracted with SVF from the reaction mixture by HC-0.8, there was also small amount of formaldehyde methyl[2,2,2-trifluoro-1-(trifluoromethyl)ethyl]acetal (compound E) found after distillation.

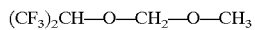
$(CF_3)_2CH—O—CH_2—O—CH_3$  E

In a typical example, the composition of products in HC-0.8 is 1% D, 63% SVF, 1% HFIP, 8% B, 15% A, and 11% C. A small amount of HFEP was removed from the extract by washing with water. Distillation of the HC-0.8 extract gives 50–57% isolated yield of SVF.

Compound A can be reintroduced to the reaction mixture (see Example 8) and become the source of more SVF. Acetal C does not survive the distillation of the HC-0.8 extract, reverting to SVF and formaldehyde (see Example 7). Ethers D, E and polyethers of the generalized formula described above would also be expected to revert to their starting materials under reaction conditions. Thus, all the significant byproducts formed by the reaction of HFIP with HF and $CH_2O$, as well as solvent and unreacted HFIP could be recycled making the new process environmentally and commercially more attractive than existing processes.

The invention will now be described in greater detail with reference to the following, non-limiting examples:

EXAMPLE 1

Preparation of SVF by Reaction/Distillation of HFIP/IF/$CH_2O$ at Atmospheric Pressure In a 0.3 L Monel reactor, equipped with a 4'×1" distillation column, a pressure gauge, thermocouple, gas outlet, liquid inlet and stirring bar, trioxane (15.0 g, 0.50 mol as $CH_2O$, 67% excess) was placed. The reactor was cooled to −30° C., evacuated, and loaded with anhydrous HF (175 g, 8.75 mol) and HFIP (56.0 g, 0.333 mol). The mixture was warmed and distillation was begun at atmospheric pressure. One hundred and five grams of material was collected at b.p. 19–20° C. More HF (139 g) was added, and the distillation was continued to give a second cut (157 g) with b.p. 19° C. Another portion of HF (157 g) was introduced, and distillation was continued to generate a third cut at 19° C. The combined distillates were analyzed by mixing a sample with water, separating the organic layer and analyzing by GC. A total of 37.4 g (0.187 mol) of SVF was isolated with the purity >99%. A pot sample was put into water, neutralized with potassium hydroxide solution, and analyzed by GC-MS with external standards showing 21.1 g (0.126 mol) of starting HFIP. Thus, the conversion was 62%, and the yield of SVF was 92%.

EXAMPLE 2

Preparation of SVF by Reaction/Distillation of HFIP/HF/$CH_2O$ at the Elevated Pressures The reactions were started as described in Example 1, but distillations were conducted at the elevated pressures (see Table 2). The distillates and the pot contents were analyzed as described above to determine amounts of unreacted HFIP remaining and SVF made.

TABLE 2

Reaction under Pressure

| | | | Reaction Conditions | | | | | |
|---|---|---|---|---|---|---|---|---|
| HF, mol | HFIP, mol | CH$_2$O, mol | Pot Temp °C. | Vapor Temp °C. | Press. psig | HF/SVF | Conv., % | SVF yield, % |
| 8.94 | 0.342 | 0.50 | 47–67 | 39–41 | 16–18 | 71:29 | 75 | 97[A] |
| 9.04 | 0.342 | 0.50 | 48–75 | 38–39 | 15–16 | 70:30 | 76 | 97[A] |
| 9.60 | 0.349 | 0.50 | 50–82 | 41–44 | 18–21 | 71:29 | 79 | 93[AB] |
| 25.2[C] | 0.817 | 0.817 | 45–62 | 43–46 | 18–22 | 75:25 | 78 | 95[A] |

[A]Purity of SVF after separating with water was 99.5+%
[B]3% acetal C was also found in the pot
[C]HFIP-trioxane mixture was added to HF refluxing at 20 psig

EXAMPLE 3

Preparation of SVF by Reaction/Distillation of HFIP/HF/CH$_2$O at Lean CH$_2$O Levels In a manner similar to Example 1, trioxane (9.0 g, 0.3 mol as CH$_2$O), HFIP (169.7 g, 1.01 mol, 237% excess HFIP), and HF (362.4 g, 18.12 mol) were loaded in a 1.0 L pot. The mixture was distilled at 18–20 psig pressure. SVF with greater than 99.5% purity, was obtained from samples washed with water. Concurrently, pot samples (~10 g) were washed with water, extracted with a mixture of tetrachlorohexafluorobutanes, Halocarbon 0.8 oil, (2×2 ml), and the extracts were analyzed by GC to monitor the reaction progress (see Table 3. After~6 h of reaction/distillation, water was added to the pot, the pot contents were neutralized with potassium hydroxide solution and distilled at atmospheric pressure to recover unreacted HFIP. Two fractions were collected with b.p. 58–60° C. (99% HFIP) and 67–98° C. (39% HFIP) having a total of 99.6 g (0.593 mol) HFIP. Conversion of HFIP was found to be 29%, and the yield of SVF 79%.

TABLE 3

Pot Analyses during Distillation of SVF

| Pot sample, No | Cumulative reaction time, h | Product Wt. % in HC-0.8 extract | | | |
|---|---|---|---|---|---|
| | | SVF | Acetals B + C | Ether A | Ether D |
| 1 | 1 | 6.6 | 1.7 | <0.1 | <0.1 |
| 2 | 2 | 3.3 | 0.5 | None | None |
| 3 | 4 | 0.3 | <0.1 | None | None |

EXAMPLE 4

Breaking the HF/SVF azeotrope (63:37) by cooling to −63° C.

| | |
|---|---|
| Starting mixture, weight | 155.8 g |
| HF/SVF ratio | 63:37 |

Upon cooling to −63° C. the volume of lower layer was about 20–25 ml. The layers were separated, weighed and each was mixed with ice water. The SVF separated from the ice water from each of the layers was collected and weighed.

| | |
|---|---|
| Lower layer, weight | 30.4 g |
| Ice-water | 140.1 g |
| SVF separated | 27.1 g |
| HF/SVF in lower layer | 11:89 |
| Upper layer, weight | 125.1 g |
| Ice-water | 377.9 g |
| SVF separated | 30.1 g |
| HF/SVF in upper layer | 76:24 |
| Total SVF from both layers, g | 57.2 g |
| SVF recovery, % 57.2/155.8 × 0.37 = | 99 |

As can be seen the HF/SVF ratio is considerably richer in SVF in the lower layer of the cooled mixture than it is at ambient temperatures. This enriched mixture is readily separated into pure SVF and the HF/SVF azeotrope by distillation.

EXAMPLE 5

Separating HF/SVF by varying the composition on the azeotrope using different pressures for distillation.

Table 4 lists the azeotrope boiling points and compositions of SVF and HF found by distillation at various pressures. The azeotrope obtained at 65 psia contains 45% SVF. A mixture of this composition can be distilled at 15 psia to obtain an azeotrope containing 20% SVF as the lower boiling component and pure SVF as the higher boiling component.

TABLE 4

SVF/HF Binary Azeotrope Composition

| | | SVF | |
|---|---|---|---|
| Temperature, °C. | Pressure, psia | Mol fraction | Weight % |
| 19 | 15 | 0.027 | 20 |
| 35 | 25 | 0.042 | 30 |
| 45 | 35 | 0.055 | 37 |
| 55 | 50 | 0.063 | 40 |
| 64 | 65 | 0.076 | 45 |

EXAMPLE 6

Preparation of SVF by fluoromethylation of HFIP with subsequent extraction with HC-0.8 oil.

A 0.3 L Monel reactor equipped with pressure gauge, thermocouple, gas outlet, liquid inlet and stirring bar was used. Trioxane (10.9 g, 0.12 mol) was placed in the reactor, which was closed, cooled to −30° C., evacuated, and loaded with anhydrous HF (36.6 g, 1.83 mol). The mixture was heated under agitation using a magnetic stirrer to 31° C., whereupon a 10 psig pressure developed. HFIP (30.3 g, 0.18 mol) was added from a bomb pressurized by $N_2$. The reactor was heated at 60–65° C. and 16–33 psig for 6 hours. A sample (7.93 g) was put into ice-water (49.7 g), and the organic layer (1.56 g) was separated and analyzed by GC. The organic mixture consisted of 5% E, 10% HFIP, 55% SVF and combined 30% of compounds A–C. The amount of SVF in the sample (0.9 g) accounted for 23% of total SVF possible.

After taking the sample, HC-0.8 (98 g, 57 ml) was added to the pot, and agitation was continued for 1 h at 60–62° C. and 38–40 psig (some $N_2$ was present in system). Ninety-five g of HC-0.8 extract was taken out, and was shown to contain 8% SVF. Another portion of HC-0.8 (70 g) was added, and the oil layer was removed after about 1 hour. The SVF content in the second extract was 5%. Reaction was continued with multiple HC-0.8 extractions until essentially no further SVF was extracted. The combined extracts, collected in 28 hours, totaled 391 g with a SVF content of 4.5%, or 18.3 g, 0.092 mol. The product composition in the extract was: 2% D, 60% SVF, 3% HFIP, 4% B, 15% C, and 13% A.

Following the extractions, the remainder (31 g) was poured into ice water. The aqueous layer was found to be 280 g. Ten g of this solution was neutralized with ammonium hydroxide to give 13.3 g of new solution, which was analyzed by GC-MS to determine the HFIP concentration. It was found to be 0.51%, with the total amount of HFIP in aqueous and HC-0.8 extract of 3.0 g, or 0.018 mol. Thus, the conversion of HFIP was 90%, and the direct SVF yield was 57%, not counting the amounts available from the byproducts.

EXAMPLE 7

Preparation of SVF by Fluoromethylation of HFIP with HC-0.8 Present from the Start In a 0.3 L Monel reactor, equipped with pressure gauge, thermocouple, gas outlet, liquid inlet and stirring bar, trioxane (32.4 g, 0.36 mol, or 1.08 mol $CH_2O$) was placed. The reactor was closed, cooled to −30° C., evacuated, and loaded with anhydrous HF (125 g, 6.25 mol). The mixture was heated to 56° C. under agitation using a magnetic stirrer, upon which 29 psig pressure was developed. HFIP (89.3 g, 0.532 mol) was added from a bomb pressurized by $N_2$ followed by HC-0.8 (70 g, 40.5 ml). The reaction was run at 60–65° C. and 50–60 psig pressure.

After about 1 h, 60 g of the HC-0.8 extract was taken out. It was found to contain 10% SVF. Another portion of HC-0.8 (71 g) was added, and the reaction was continued removing several portions of the oil and approximately replacing those portions at 60–65° C. until essentially no SVF was found in the extract. The combined extracts weighed 1228 g and had a SVF content of 3.7%. The composition of all the products was: 1% D, 1% HFIP, 63% SVF, 8% B, 11% C, and 15% A.

Distillation of 1,123 g of HC-0.8 extract after washing with $NH_4OH$ and drying over $SiO_2$ afforded: 42.8 g of product with b.p. 58–59° C., consisted of 99.7% SVF and traces of B and E; 18.6 g in the second cut, with b.p. 70–130° C., consisted of 9% SVF, 29% B, 58% HC-0.8, and a trace of E. While taking the second cut there was deposition of white crystalline product (polymer of $CH_2O$) in the condenser. No C was found in the distilled material or in the pot. The total amount of SVF based on the original HC-0.8 solution was 48.7 g, or 0.243 mol. The amount of unreacted HFIP was 8.4 g, or 0.05 mol that accounted for 91% conversion and 50% yield of SVF, based on consumed HFIP but not taking into account the SVF recoverable from the byproducts.

EXAMPLE 8

Preparation of SVF by Reaction of A with HF

To a 0.3 L Monel reactor equipped with a pressure gauge, thermocouple, gas outlet, liquid inlet and stirring bar, A (20.6 g, 0.054 mol) was added. The reactor was closed, cooled to −30° C., evacuated, and loaded with anhydrous HF (25 g, 1.25 mol) and HC-0.8 (44 g), and the reaction mixture was heated to 60–70° C. After 1.5 h an HC-0.8 extract (28 g) was taken out, and the reaction was continued under multiple extraction conditions, as described in Example 7. A total 284 g of HC-0.8 extract was collected with a SVF content of 3.9% that accounted for 11.1 g, or 0.055 mol of material. Based on the content of A in the HC-0.08 solution (0.3%), the conversion was found to be 96%, and the yield of SVF 53%.

It will be appreciated that the instant specification and claims are set forth by way of illustration and not limitation, and that various modifications and changes may be made without departing from the spirit and scope of the present invention.

What is claimed is:

1. A process for preparing fluoromethyl 2,2,2-trifluoro-1-(trifluoromethyl)ethyl ether(sevoflurane) comprising the following steps:

a) reacting a mixture comprising 1,1,1,3,3,3-hexafluoro-2-propanol (HFIP), formaldehyde and hydrogen fluoride to form sevoflurane;

b) distilling off from the reacting mixture an azeotrope of sevoflurane and hydrogen fluoride substantially free of HFIP; and c) separating sevoflurane from the azeotrope.

2. The process according to claim 1, which comprises reacting HFIP, formaldehyde and a stoichiometric excess of hydrogen fluoride.

3. The process according to claim 1, which is conducted at elevated pressures.

4. The process according to claim 1, which further comprises converting byproducts of the reacting to sevoflurane, said byproducts being selected from the group consisting of bis{[2,2,2-trifluoro-1-(trifluoromethyl)ethoxy]methyl}ether, formaldehyde di[2,2,2-trifluoro-1-(trifluoromethyl)ethyl] acetal, formaldehyde fluoromethyl[2,2,2-trifluoro-1-(tifluoromethyl)ethyl]acetal, formaldehyde methyl[2,2,2-trifluoro-1-(trifluoromethyl)ethyl]acetal, and bis (fluoromethyl)ether, and said converting comprising maintaining the byproducts under reacting conditions or recycling the byproducts to the reacting.

5. The process according to claim 1, wherein sevoflurane is separated from its hydrogen fluoride azeotrope by solvent extraction with a solvent capable of selectively extracting sevoflurane.

6. The process according to claim 5, wherein the solvent is selected from the group consisting of chlorofluorocarbons, chlorohydrocarbons, perfluorohydrocarbons, perfluoroethers and hydrocarbons.

7. The process according to claim 6, wherein the solvent is selected from the group consisting of tetrachlorohexafluorobutanes.

8. The process according to claim 7, wherein the solvent is HC-0.8 oil.

9. The process according to claim 1, wherein sevoflurane is separated from its hydrogen fluoride azeotrope by cooling and as a result of said cooling establishing two layers, one of which is enriched in sevoflurane from which purer sevoflurane can be obtained by distillation.

10. The process according to claim 1, wherein sevoflurane is separated from its hydrogen fluoride azeotrope by distillation at one pressure to obtain a different content azeotrope from which purer sevoflurane can be obtained by distillation at another pressure.

11. The process according to claim 1, wherein water is removed from the reacting mixture as a constant boiling mixture, with hydrogen fluoride.

12. The process according to claim 1, wherein said mixture comprises one or more polyethers of the general formula $R_1O(CH_2O)nR_2$, where n is 1 or 2 and $R_1$ and $R_2$ are independently selected from the group consisting of hydrogen, alkyl groups, and haloalkyl groups, but both $R_1$ and $R_2$ are not hydrogen in the same formula.

13. A process for preparing fluoromethyl 2,2,2-trifluoro-1-(trifluoromethyl)ethyl ether(sevoflurane) comprising reacting a mixture comprising 1,1,1,3,3,3-hexafluoro-2-propanol (HFIP), formaldehyde and hydrogen fluoride under distillation in the absence of a dehydrating, protonating or fluoride ion generating agent.

14. The process according to claim 13, comprising reacting 1,1,1,3,3,3-hexafluoro-2-propanol with formaldehyde and a stoichiometric excess of hydrogen fluoride under distillation.

15. The process according to claim 13, which is conducted at elevated pressures.

16. The process according to claim 13, wherein sevoflurane is removed from the reacting mixture by distillation as an azeotrope with hydrogen fluoride.

17. The process according to claim 13, which further comprises converting byproducts of the reacting to sevoflurane, said byproducts being selected from the group consisting of bis{[2,2,2-trifluoro-1-(trifluoromethyl)ethoxy]methyl}ether, formaldehyde di[2,2,2-trifluoro-1-(trifluoromethyl)ethyl]acetal, formaldehyde fluoromethyl[2,2,2-trifluoro-1-(trifluoromethyl)ethyl]acetal, formaldehyde methyl[2,2,2-trifluoro-1-(trifluoromethyl)ethyl]acetal, and bis(fluoromethyl) ether, and said converting comprising maintaining the byproducts under reaction conditions or recycling the byproducts to the reacting.

18. The process according to claim 13, wherein sevoflurane is separated from its hydrogen fluoride azeotrope by solvent extraction.

19. The process according to claim 18, wherein the solvent is selected from the group consisting of chlorofluorocarbons, chlorohydrocarbons, perfluorohydrocarbons, perfluoroethers and hydrocarbons.

20. The process according to claim 19, wherein the solvent is selected from the group consisting of tetchlorohexafluorobutanes.

21. The process according to claim 20, wherein the solvent is HC-0.8 oil.

22. The process according to claim 13, wherein sevoflurane is separated from hydrogen fluoride by cooling and as a result of said cooling establishing two layers, one of which is enriched in sevoflurane from which purer sevoflurane can be obtained by distillation.

23. The process according to claim 13, wherein sevoflurane is separated from its hydrogen fluoride azeotrope by distillation at one pressure to obtain a different content azeotrope from which purer sevoflurane can be obtained by distillation at another pressure.

24. The process according to claim 13, wherein water is removed from the reacting mixture as a constant boiling mixture with hydrogen fluoride.

25. The process according to claim 13, wherein said mixture comprises one or more polyethers of the general formula $R_1O(CH_2O)nR_2$, where n is 1 or 2 and $R_1$ and $R_2$ are independently selected from the group consisting of hydrogen, alkyl groups, and haloalkyl groups, but both $R_1$ and $R_2$ are not hydrogen in the same formula.

26. A process for preparing fluoromethyl 2,2,2-trifluoro-1-(trifluoromethyl)ethyl ether(sevoflurane) comprising reacting a mixture comprising 1,1,1,3,3,3-hexafluoro-2-propanol (HFFP), formaldehyde and hydrogen in the presence of or with the subsequent addition of a solvent capable of selectively extracting sevoflurane.

27. A process according to claim 26 for preparing fluoromethyl 2,2,2-trifluoro-1-(trifluoromethyl)ethyl ether (sevoflurane) comprising reacting a mixture comprising 1,1,1,3,3,3-hexafluoro-2-propanol (HFIP), formaldehyde and hydrogen fluoride in the presence of or with the subsequent addition of a non-aqueous solvent capable of selectively extracting sevoflurane.

28. A process for preparing fluoromethyl 2,2,2-trifluoro-1-(trifluoromethyl)ethyl ether(sevoflurane) comprising reacting a mixture comprising 1,1,1,3,3,3-hexafluoro-2-propanol (HFIP), formaldehyde and hydrogen fluoride in the absence of a dehydrating, protonating or fluoride ion generating agent, but in the presence of or with the subsequent addition of a solvent capable of selectively extracting sevoflurane.

29. A process for preparing fluoromethyl 2,2,2-trifluoro-1-(trifluoromethyl)ethyl ether(sevoflurane) comprising reacting a mixture comprising 1,1,1,3,3,3-hexafluoro-2-propanol (HFIP), formaldehyde and hydrogen fluoride in the presence of or with the subsequent addition of a solvent capable of selectively extracting sevoflurane, said solvent being selected from the group consisting of chlorofluorocarbons, chlorohydrocarbons, perfluorohydrocarbons, perfluoroethers and hydrocarbons.

30. The process according to claim 29, wherein the solvent capable of selectively extracting sevoflurane is HC-0.8 oil.

31. The process according to claim 30, which comprises:
a) reacting HFIP with formaldehyde and hydrogen fluoride in the presence of or with the subsequent addition of HC-0.8 oil to yield a HC-0.8 oil solution comprising sevoflurane, bis{[2,2,2-trifluoro-1-(trifluoromethyl) ethoxy]methyl}ether, formaldehyde di[2,2,2-trifluoro-1-(trifluoromethyl)ethyl]acetal, formaldehyde methyl [2,2,2-trifluoro-1-(trifluoromethyl)ethyl]acetal and formaldehyde fluoromethyl[2,2,2-trifluoro-1-(trifluoromethyl)ethyl]acetal;
b) separating sevoflurane from said HC-0.8 oil solution by distillation to yield sevoflurane and residual HC-0.8 oil solution; and
c) recycling said residual HC-0.8 oil solution to the process.

32. It The process according to claim 31, which further comprises preparing sevoflurane by reacting said bis {[2,2,2-trifluoro-1-(trifluoromethyl)ethoxy]methyl}ether with hydrogen fluoride in the presence of or with the addition of a solvent capable of selectively extracting sevoflurane.

33. The process according to claim 32, wherein the solvent capable of selectively extracting sevoflurane is selected from the group consisting of chlorofluorocarbons, chlorohydrocarbons, perfluorohydrocarbons, perfluoroethers and hydrocarbons.

34. The process according to claim 33, wherein the solvent capable of selectively extracting sevoflurane is HC-0.8 oil.

35. The process according to claim 31, which further comprises preparing sevoflurane by reacting said formaldehyde di[2,2,2-trifluoro-1-(trifluoromethyl)ethyl]acetal, and said formaldehyde fluoromethyl[2,2,2-trifluoro-1-(trifluoromethyl)ethyl]acetal with hydrogen fluoride and formaldehyde in the presence or with the addition of a solvent capable of selectively extracting sevoflurane.

36. The process according to claim 35, wherein the solvent capable of selectively extracting sevoflurane is selected from the group consisting of chlorofluorocarbons, chlorohydrocarbons, perfluorohydrocarbons, perfluoroethers and hydrocarbons.

37. The process according to claim 36, wherein the solvent capable of selectively extracting sevoflurane is HC-0.8 oil.

38. The process according to claim 29, wherein said mixture comprises one or more polyethers of the general formula $R_1O(CH_2O)nR_2$, where n is 1 or 2 and $R_1$ and $R_2$ are independently selected from the group consisting of hydrogen, alkyl groups, and haloalkyl groups, but both $R_1$ and $R_2$ are not hydrogen in the same formula.

39. A process for separating fluoromethyl 2,2,2-trifluoro-1-(trifluoromethyl)ethyl ether(sevoflurane) from a mixture comprising sevoflurane,1,1,1,3,3,3-hexafluoro-2-propanol (BFIP) and hydrogen fluoride, said process comprising:
a) providing a mixture comprising sevoflurane, HFIP and hydrogen fluoride;
b) distilling off from said mixture an azeotrope of sevoflurane and hydrogen fluoride substantially free of HFIP; and
c) separating sevoflurane from said azeotrope.

40. A process for separating fluoromethyl 2,2,2-trifluoro-1-(trifluoromethyl)ethyl ether(sevoflurane) from a mixture comprising sevoflurane, 1,1,1,3,3,3-hexafluoro-2-propanol (HEIP) and hydrogen fluoride, said process comprising:
a) providing a mixture comprising sevoflurane, HFIP and hydrogen fluoride; and
b) extracting with a solvent capable of selectively extracting sevoflurane.

41. A process for preparing fluoromethyl 2,2,2-trifluoro-1-(tifluoromethyl)ethyl ether(sevoflurane) comprising the following steps:
a) reacting a mixture comprising 1,1,1,3,3,3-hexafluoro-2-propanol (HFIP), formaldehyde and hydrogen fluoride to form sevoflurane;
b) subjecting the reacting mixture to fractional distillation to recover a fractional distillate comprising sevoflurane and hydrogen fluoride substantially free of HFIP.
c) recovering purer sevoflurane from the fractional distillate.

\* \* \* \* \*

UNITED STATES PATENT AND TRADEMARK OFFICE
CERTIFICATE OF CORRECTION

PATENT NO. : 6,469,219 B1
DATED : October 22, 2002
INVENTOR(S) : Achot Pavlikovich Khrimian et al.

It is certified that error appears in the above-identified patent and that said Letters Patent is hereby corrected as shown below:

Column 10,
Line 62, "(trifluoromethyl)" should read -- (trifluoromethyl") --.

Column 11,
Line 26, "mixture, with" should read -- mixture with --.

Column 12,
Line 32, "(HFFP)" should read -- (HFIP) --.

Column 13,
Line 16, delete "iI".

Column 14,
Line 13, "(BFIP)" should read -- (HFIP) --.
Line 23, "(HEIP)" should read -- (HFIP) --.
Line 29, "tifluoromethyl" should read -- trifluoromethyl --.
Line 36, "free of HFIP" should read -- free of HFIP; and --.

Signed and Sealed this

Tenth Day of August, 2004

JON W. DUDAS
*Acting Director of the United States Patent and Trademark Office*